(12) United States Patent
Finkelstein

(10) Patent No.: US 6,777,554 B2
(45) Date of Patent: Aug. 17, 2004

(54) PREPARATION OF N-METHYLPAROXETINE AND RELATED INTERMEDIATE COMPOUNDS

(75) Inventor: Nina Finkelstein, Herzliya (IL)

(73) Assignee: Teva Pharmaceutical Industries Ltd., Petah Tiova (IL)

( * ) Notice: Subject to any disclaimer, the term of this patent is extended or adjusted under 35 U.S.C. 154(b) by 0 days.

(21) Appl. No.: 10/067,160

(22) Filed: Feb. 4, 2002

(65) Prior Publication Data

US 2002/0151567 A1 Oct. 17, 2002

Related U.S. Application Data

(60) Provisional application No. 60/277,587, filed on Mar. 21, 2001, and provisional application No. 60/266,498, filed on Feb. 5, 2001.

(51) Int. Cl.$^7$ ..................... C07D 405/12; A61K 31/445
(52) U.S. Cl. ....................................... 546/197; 514/321
(58) Field of Search ........................... 546/197; 514/321

(56) References Cited

U.S. PATENT DOCUMENTS

| | | | |
|---|---|---|---|
| 3,912,743 A | 10/1975 | Christensen et al. | 546/197 |
| 4,007,196 A | 2/1977 | Christensen et al. | 546/197 |
| 4,585,777 A | 4/1986 | Lassen et al. | 514/317 |
| 4,902,801 A | 2/1990 | Faruk et al. | 546/220 |
| 5,019,582 A | 5/1991 | Drejer et al. | 514/321 |
| 5,039,803 A | 8/1991 | Smith et al. | 546/185 |
| 5,081,128 A | 1/1992 | George et al. | 514/323 |
| 5,096,900 A | 3/1992 | George et al. | 514/213 |
| 5,179,108 A | 1/1993 | George et al. | 514/319 |
| 5,258,517 A | 11/1993 | Zepp et al. | 546/240 |
| 5,948,914 A | 9/1999 | Sugi et al. | 546/240 |
| 6,004,990 A | 12/1999 | Elmaleh et al. | 514/415 |
| 6,066,737 A | 5/2000 | Adger et al. | 546/240 |
| 6,326,496 B1 | 12/2001 | Brennan | 546/240 |
| 6,433,179 B1 | 8/2002 | Wang et al. | 546/197 |
| 6,657,062 B1 | 12/2003 | Kreidl et al. | 546/197 |
| 2003/0065172 A1 * | 4/2003 | Tian et al. | 544/3 |
| 2003/0083501 A1 * | 5/2003 | Avrutov et al. | 546/197 |
| 2003/0125560 A1 | 7/2003 | Hoom et al. | |

FOREIGN PATENT DOCUMENTS

| | | |
|---|---|---|
| WO | WO 02/06275 | 1/2002 |

OTHER PUBLICATIONS

Tian et al. "Synthesis of acesulfam potassium" Ca 138:287704 (2003).*
Chapman et al. "Crystal structure and thermodynamics of . . . " CA 129:122262 (1998).*
Database CAPLUS on STN (Columbus, OH, USA) Accession No. 1995:339464, Agafonova et al., "Method of preparing alcohol of phenol difluoromethy ethers," DN. 122:132748, SU 1816754, 1993.

* cited by examiner

Primary Examiner—Celia Chang
(74) Attorney, Agent, or Firm—Kenyon & Kenyon

(57) ABSTRACT

The present invention provides a process for preparing N-methylparoxetine, an intermediate in the synthesis of paroxetine, by reacting sesamol-tetrabutylammonium salt with CIPMA. The present invention is not limited to the synthesis of N-methylparoxetine, but also includes other similar compounds.

33 Claims, No Drawings

PREPARATION OF N-METHYLPAROXETINE AND RELATED INTERMEDIATE COMPOUNDS

CROSS REFERENCE

The present invention claims priority under 35 U.S.C. 1.119 (e) to U.S. Appl. No. 60/277,587, filed on Mar. 21, 2001, and U.S. Appl. No. 60/266,498, filed on Feb. 5, 2001, both entitled "Process for the Preparation of N-methylparoxetine."

FIELD OF THE INVENTION

The field of the invention is synthesis of paroxetine and like compounds, more specifically the preparation of an intermediate in the synthesis of paroxetine.

BACKGROUND OF THE INVENTION

Paroxetine, trans (−)-3-[(1,3-benzodioxol-5-yloxy) methyl]-4-(4-fluorophenyl) piperidine, is a serotonin re-uptake inhibitor, and has the following molecular formula:

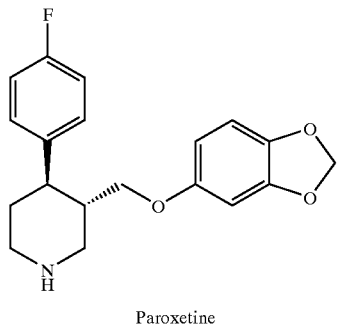

Paroxetine

Paroxetine is an orally administered antidepressant for the treatment of depression, social anxiety disorders, obsessive compulsive disorder, panic disorder, social anxiety disorder, generalized anxiety disorder and posttraumatic stress disorder. Paroxetine is marketed as Paxil® by GlaxoSmithKline.

Paxil® is prescribed as oral dosage tablets containing 10 mg, 20 mg, 30 mg and 40 mg of the base equivalent of paroxetine hydrochloride. Paxil® tablets include dibasic calcium phosphate dihydrate, hydroxypropyl methylcellulose, magnesium stearate, polyethylene glycols, polysorbate 80, sodium starch glycolate, titanium dioxide and one or more of the following: D&C Red No. 30, D&C Yellow No. 10, FD&C Blue No. 2, FD&C Yellow No. 6.

Paxil® is also available as an oral suspension with a dosage of 10 mg of the base equivalent of paroxetine hydrochloride in a 5 mL suspension containing polacrilin potassium, microcrystalline cellulose, propylene glycol, glycerin, sorbitol, methyl paraben, propyl paraben, sodium citrate dihydrate, citric acid anhydrate, sodium saccharin, flavorings, FD&C Yellow No. 6 and simethicone emulsion, USP.

Paroxetine may be produced by synthesizing an intermediate, N-methylparoxetine, wherein the methyl group is attached to the amine of the piperidine group. In paroxetine, the amine is a secondary amine, while in the intermediate, the amine is a tertiary amine.

U.S. Pat. Nos. 4,007,196, 5,258,517 and 4,585,777, incorporated herein by reference, disclose the conversion of N-methylparoxetine to paroxetine. The methyl group is removed by reaction with phenyl chloroformate followed by deacylation with a base such as KOH to obtain paroxetine.

N-methylparoxetine has the following structure (II):

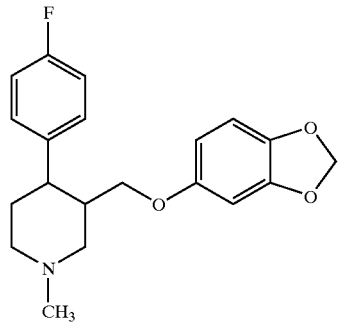

The '196 patent discloses obtaining N-methylparoxetine by reacting 4-(4-fluorophenyl)-3-chloromethyl-N-methyl-piperidine, also named CIPMA of structure (III):

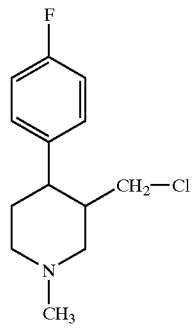

with 3,4-methylenedioxyphenol ("sesamol") of structure (IV):

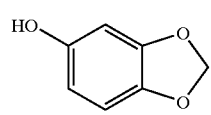

to obtain N-methylparoxetine. U.S. Pat. No. 4,007,196 reacts CIPMA with sesamol in a solution of sodium in methanol, giving N-methylparoxetine with a yield of about 25%.

U.S. Pat. No. 4,585,777, is directed to the composition 4-(4-fluorophenyl)-3-((4-methoxyphenoxy)-methyl)-piperidine, which has the structure of:

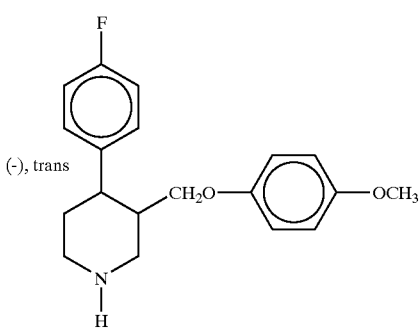

To obtain the product, the '777 patent first prepares an N-methyl intermediate by reacting in examples 5 and 8 the sulfonate esters of the enantiomers of cis-4-(4-fluorophenyl)-3-hydroxymethyl-1-methylpiperidine with p-methoxyphenol. The '777 patent does not give a yield for example 5. For example 8, 38.5 grams of the ester were used to obtain 1.8 grams of the product as a free base, giving a yield of about 5%.

Much of the prior art is directed to synthesis of CIPMA, related compounds and their precursors, rather than synthesis of N-methylparoxetine from CIPMA. For example, U.S. Pat. No. 6,326,496, incorporated herein by reference, teaches obtaining CIPMA by reducing a precursor through the use of a metal hydride. These patents provide little insight on how to synthesize N-methylproxetine after obtaining CIPMA, or how to increase the yield of such synthesis.

The low yield of N-methylparoxetine produced results in lower yields of paroxetine. The low yield increases the cost of the process and requires additional purification.

A need exists in the art to produce N-methylparoxetine and related compounds with a reaction that produces a high yield.

SUMMARY OF THE INVENTION

The present invention provides a process for preparing compound (VII) comprising reacting compound (V) with compound (VI) in an organic solvent:

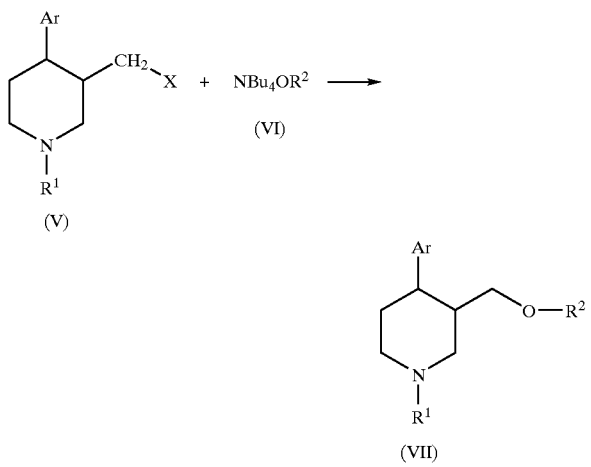

wherein:
X is selected from the group consisting of halogen and —OSO2R$^3$;
Ar is phenyl optionally substituted by halogen, alkoxy or other inert group;

R$^1$ is selected from the group consisting of hydrogen, alkyl, aralkyl, alkaryl, alkyloxycarbonyl, axyloxycarbonyl and arylalkoxycarbonyl;
R$^2$ is selected from the group consisting of aryl and heteroaryl, wherein any one or more of said aryl and heteroaryl are optionally substituted by the group consisting of alkyl, halogen, alkoxy, nitro, acylamino, methylenedioxy, alkyl sulfonyl, aryl sulfonyl, alkaryl sulfonyl and aralkyl sulfonyl, and
R$^3$ is selected from the group consisting of alkyl, aryl, aralkyl and alkaryl.

In another aspect, the present invention provides a process for preparing N-methylparoxetine comprising reacting CIPMA with sesamol-tetrabutylammonium salt in an organic solvent.

In another aspect, the present invention provides for sesamol-tetrabutylammonium salt.

DETAILED DESCRIPTION OF THE INVENTION

The term "yield" as used herein refers to the moles of the intermediate obtained (VII) (preferably N-methylparoxetine) compared to the moles of compound (V) (preferably CIPMA) used.

The term "NBu$_4$" as used herein refers to tetrabutylammonium ion.

Attempts by the Applicant to produce a reaction with a high yield, other than the present invention, have failed. CIPMA and sesamol were reacted in the presence of polar solvents such as dimethylformamide, acetone or methylethylketone and strong bases such as sodium hydroxide, sodium methoxide and potassium tert-butoxide, and nonpolar solvents such as toluene, dichloromethane or methyl-iso-butyl ketone in liquid—liquid PTC (phase transfer catalysis) reactions.

CIPMA was also reacted by the Applicant with sesamol in liquid-solid PTC reactions in the presence of solvents such as toluene or acetonirile. The PTC reactions were performed in the presence of bases such as sodium hydroxide, potassium hydroxide, potassium carbonate or barium hydroxide. Tetrabutylammonium bromide and tricaprylmethylammonium chloride, tributylbenzylammonium bromide, PEG 400 were used as PTC catalysts. However all of above described experiments, carried out by the Applicant, gave low yields of N-methylparoxetine and complex mixture of products including mostly CIPMA.

The present invention provides a process for producing N-methylparoxetine and similar intermediates with reactions that result in a higher yield than that obtained in the prior art. Specifically, the process of the present invention obtains a yield of about 86%, which is much higher than the 25% yield of the prior art.

The present invention is directed to the use of sesamol-tetrabutylammonium salt to increase the yield of N-methylparoxetine obtained. The salt may be prepared by dissolving sesamol and tetrabutylammonium hydroxide in an alcohol or a mixture of alcohols. Preferably the alcohol used is a mixture of isopropanol and methanol. The solvents are then evaporated, preferably under reduced pressure to obtain a residue, the salt. One skilled in the art may appreciate that instead of adding tetrabutylamonium hydroxide, a salt of tetrabutylammonium, such as the bromide salt, may be added in conjunction with a base, such as sodium hydroxide.

The salt is added to a mixture of CIPMA and a solvent such as acetonitrile, toluene or isopropanol. The reaction mixture comprising CIPMA, sesamol-tetrabutylammonium salt and a solvent is preferably heated for a few hours, most preferably for about 4 hours at reflux. The reaction mixture is then cooled and the solvent is removed to obtain a residue. Preferably the solvent is removed by evaporation under reduced pressure.

The residue is then dissolved in an organic solvent, such as toluene and is washed with a polar solvent such as water and a base such as sodium hydroxide. The reaction mixture is then dried by using a drying agent such as sodium sulfate and the solvent is evaporated to obtain N-methylparoxetine. The present invention obtains a yield of about 86%, more than 3 times that of the prior art.

The present invention provides a process for preparing compound (VII) comprising reacting compound (V) with compound (VI) in an organic solvent:

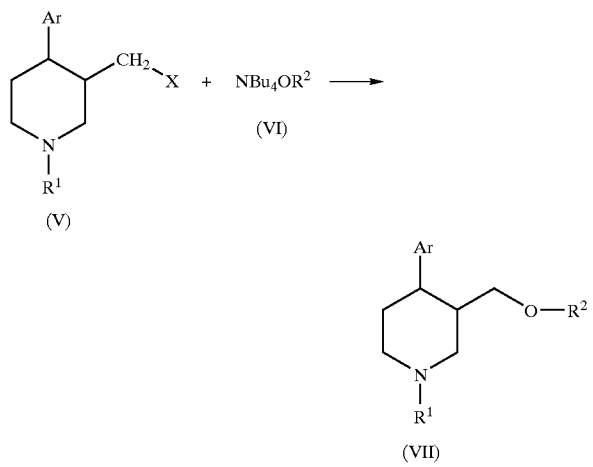

wherein

X is selected from the group consisting of halogen and —OSO2R$^3$;

Ar is phenyl optionally substituted by halogen, alkoxy or other inert group;

R$^1$ is selected from the group consisting of hydrogen, alkyl, aralkyl, alkaryl, alkyloxycarbonyl, aryloxycarbonyl and arylalkoxycarbonyl;

R$^2$ is selected from the group consisting of aryl and heteroaryl, wherein any one or more of said aryl and heteroaryl are optionally substituted by the group consisting of alkyl, halogen, alkoxy, nitro, acylamino, methylenedioxy, alkyl sulfonyl, aryl sulfonyl, alkaryl sulfonyl and aralkyl sulfonyl; and R$^3$ is selected from the group consisting of alkyl, aryl, aralkyl and alkaryl.

CIPMA can be obtained by using a metal hydride, such as lithium aluminum hydride, to reduce an ester to an alcohol, as taught in U.S. Pat. No. 4,007,196. The formed alcohol is a precursor of CIPMA. The alcohol is then converted to an alkyl halide because a halogen is a better leaving group than a hydroxide group.

The present invention uses a leaving group which is preferably either a halogen or a sulfonyl group. A hydroxide group is not a good leaving group, which makes its conversion to a halogen or a sulfonyl group necessary. A sulfonyl compound is often used to convert an alcohol to a sulfonate ester.

The sulfonyl compounds which may be used to convert the alcohol into a sulfonate ester are for example a typical sulfonyl chloride such as trifluoromethanesulfonyl chloride and p-toluenesulfonyl chloride. Pyridine is generally used as a solvent in such reactions in order to neutralize the formed hydrochloric acid, a byproduct of the reaction.

The present invention prefers the use of halogens as a leaving group. The most preferred halogen is chlorine, with others being iodine and bromine. The leaving group in CIPMA is a chlorine.

The conversion of an alcohol to an alkyl halide is well known in the art. Phosphorous tribromide (PBr$_3$), phosphorous trichloride (PCl$_3$) and thionyl chloride (SOCl$_2$) may be used to convert the alcohol into an alkyl halide. Pyridine may be used as a solvent to neutralize any formed hydrochloric acid.

The present invention reacts compound (V) with compound (VI). Compound (V) comprises of a piperidine and an aryl group. The aryl group of compound (V) may be substituted with a halogen, an alkoxy group or other inert groups. Other inert group refers to homologs of benzene, where by replacing a hydrogen on the aryl group with a CH$_3$ or higher alkyl groups, a series of homologs may be made, such as toluene or ethylbeuzene. Preferably, the aryl group of compound (V) is substituted with a fluorine. The most preferable embodiment of the present invention has the fluorine in a para position because the fluorine is in the para position in paroxetine. (See compound (I)).

Groups that may be connected to the amine of the piperidine in compound (V) may include hydrogen, alkyl, aralkyl, alkaryl, alkyloxycarbonyl, aryloxycarbonyl and arylalkoxycarbonyl. These groups, other than the hydrogen, act as protecting groups, by preventing reactions involving the amine group. Alkyls, particularly methyl groups are preferred. One skilled in the art may appreciate that other protecting groups known in the art may be used, and that the particular group used may not necessarily affect the result.

The present invention optionally and preferably removes the protecting group. For example, the methyl group of N-methylparoxetine may be removed by transformation to carbamate followed by alkaline hydrolysis. To obtain the carbamate, N-methylparoxetine may be reacted with phenyl chloroformate. The formed carbamate is then treated with a base such as KOH. One skilled in the art may appreciate that if compound (V) is substituted with a hydrogen, a subsequent deacylation step is unnecessary. Such reaction however should be carried out under conditions where the secondary amine does not react undesirably with other groups.

Compound (VI) of the present invention may comprise of an aryl or a heteroaryl, which is optionally substituted by the group consisting of alkyl, halogen, alkoxy, nitro, acylamino, methylenedioxy, alkyl sulfonyl, aryl sulfonyl and alkaryl sulfonyl. Sesamol has an aryl group which is substituted by methylenedioxy. One skilled in the art may appreciate that sesamol is the most preferred embodiment of the present invention because it leads to formation of N-methylparoxetine. The scope of the claims however are broader than sesamol and cover compounds with aryl and heteroaryl groups which are optionally substituted with groups other than methylenedioxy.

The most preferred embodiment of the present invention provides a process for preparing N-methylparoxetine comprising reacting CIPMA with sesamol-tetrabutylammonium salt (compound VIII) in an organic solvent.

In one preferred embodiment, the organic solvent is an aprotic polar solvent. Most preferably, the aprotic polar solvent is acetonitrile.

The present invention however is not limited to the use of an aprotic polar solvent to achieve high yields. The present invention also obtains high yields by use of protic and non-polar solvents.

In one embodiment, the present invention uses aromatic solvents. Preferably, the aromatic solvent used is toluene. Other solvents with relatively the same polarity as toluene are preferred. The yield of the present invention using toluene as a solvent was about 86%.

The present invention also uses an alcohol to carry out the reaction. Preferably the alcohol is a $C_1$ to a $C_6$ alcohol. Most preferably, the alcohol used is isopropanol. One skilled in the art may appreciate that the use of a particular solvent is not essential to the present invention. Other solvents that may be used include esters of fatty acids, aliphatic hydrocarbons and ethers.

One skilled in the art may appreciate that the particular stereoisomer obtained plays a critical role in the effectiveness of a drug. The most preferred stereoisomers are those arranged like paroxetine.

The following examples are given for illustration.

EXAMPLES

Preparation of N-methylparoxetine

Example 1

Sesamol (4.32 g, 31.2 mmol) was added to a solution of tetrabutylammonium hydroxide in isopropanol/methanol (0.1N, 342 mL), and the solvents were evaporated under vacuum to dryness. The residual tetrabutylammonium salt of sesamol was dissolved in acetonitrile (40 mL) and 4-(4-fluorophenyl)-3-chloromethyl-N-methyl-piperidine (CIPMA) (7.5 g, 31.2 mmol) was added. The reaction mixture was stirred with heating at reflux for 4 hours. After cooling, the reaction mixture was evaporated to dryness in vacuum and the residue was dissolved in toluene. The toluene solution was washed with 5% aq. sodium hydroxide and then with water. After drying with sodium sulfate and evaporation of the solvent in vacuum, N-methylparoxetine (8.1 grams) was obtained with yield 76%.

Example 2

Sesamol (4.76 g, 34.2 mmol) was added to a solution of tetrabutylammonium hydroxide in isopropanol/methanol (0.1 N, 342 mL), and the solvents were evaporated under vacuum to dryness. The residual tetrabutylammonium salt of sesamol was dissolved in acetonitrile (40 mL) and 4-(4-fluorophenyl)-3-chloromethyl-N-methyl-piperidine (CIPMA) (7.5 g, 31.2 mmol) was added. The reaction mixture was stirred with heating at reflux for 4 hrs. After cooling, the reaction mixture was evaporated to dryness in vacuum and the residue was dissolved in toluene. The toluene solution was washed with 5% aq. sodium hydroxide and then with water. After drying with sodium sulfate and evaporation of the solvent in vacuum N-methylparoxetine (9.2 grams) was obtained with yield 86%.

Example 3

Sesamol (4.76 g, 34.2 mmol) was added to a solution of tetrabutylammonium hydroxide in isopropanol/methanol (0.1N, 342 mL), and the solvents were evaporated under vacuum to dryness. The residual tetrabutylammonium salt of sesamol was dissolved in toluene (40 mL) and 4-(4-fluorophenyl)-3-chloromethyl-N-methyl-piperidine (CIPMA) 7.5 g (31.2 mmol) was added. The reaction mixture was stirred with heating at reflux for 4 hrs. After cooling, the reaction mixture was washed with 5% aq. sodium hydroxide and then with water. After drying with sodium sulfate and evaporation of the solvent in vacuum N-methylparoxetine (9.1 grams) was obtained with yield 85%.

Example 4

Sesamol (4.76 g, 34.2 mmol) was added to a solution of tetrabutylammonium hydroxide in isopropanol/methanol (0.1N, 342 mL), and the solvents were evaporated under vacuum to dryness. The residual tetrabutylammonium salt of sesamol was dissolved in isopropyl alcohol (40 mL) and 4-(4-fluorophenyl)-3-chloromethyl-N-methyl-piperidine (CIPMA) 7.5 g (31.2 mmol) was added. The reaction mixture was stirred with heating at reflux for 4 hrs. After cooling, the reaction mixture was evaporated to dryness in vacuum and the residue was dissolved in toluene. The solution was washed with 5% aq. sodium hydroxide and then with water. After drying with sodium sulfate and evaporation of the solvent in vacuum N-methylparoxetine (8.3 grams) was obtained with yield 78%.

Having thus described the invention with reference to particular preferred embodiments and illustrated it with examples, those in the art may appreciate modifications to the invention as described and illustrated that do not depart from the spirit and scope of the invention as disclosed in the specification.

What is claimed is:

1. A process for preparing compound (VII) comprising reacting

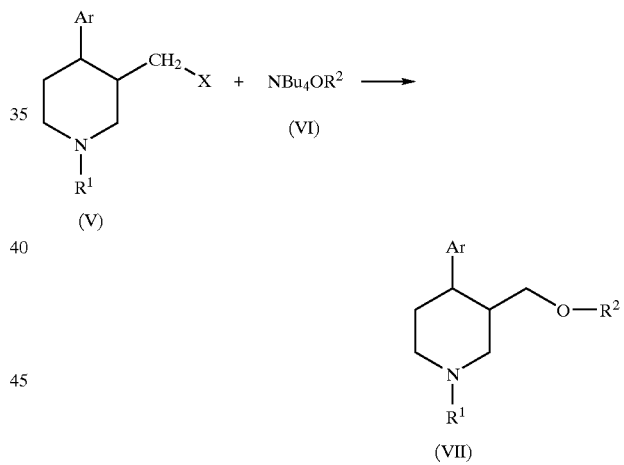

compound (V) with compound (VI) in an organic solvent: wherein

X is selected from the group consisting of halogen and $-OSO_2R^3$;

Ar is phenyl optionally substituted by halogen, alkoxy or other inert group;

$R^1$ is selected from the group consisting of hydrogen, alkyl, aralkyl, alkaryl, alkyloxycarbonyl, aryloxycarbonyl and aryl alkoxycarbonyl;

$R^2$ is selected from the group consisting of aryl and heteroaryl, wherein any one or more of said aryl and heteroaryl are optionally substituted by the group consisting of alkyl, halogen, alkoxy, nitro, acylamino, methylenedioxy, alkyl sulfonyl, aryl sulfonyl, alkaryl sulfonyl and aralkyl sulfonyl; and $R^3$ is selected from the group consisting of alkyl, aryl, aralkyl and alkaryl.

2. The process of claim 1 wherein $R^1$ is methyl, Ar is fluorophenyl and X is selected from a group consisting of halogen, mesylate and tosylate.

3. The process of claim 2, wherein the fluorophenyl has a fluorine in a para position.

4. The process of claim 1, wherein the organic solvent is selected from the group consisting of toluene and isopropyl alcohol.

5. The process of claim 1, wherein the organic solvent is a dipolar aprotic solvent.

6. The process of claim 5, wherein the dipolar aprotic solvent is acetonitrile.

7. The process of claim 1, wherein the yield is at least about 25%.

8. The process of claim 7, wherein the yield is at least about 55%.

9. The process of claim 8, wherein the yield is at least about 85%.

10. The process of claim 1, further comprising a step of replacing $R^1$ with a hydrogen in compound (VII).

11. The process of claim 10, wherein $R^1$ is a methyl group.

12. The process of claim 11, wherein the methyl group is removed by transformation to a carbamate followed by alkaline hydrolysis.

13. A process for preparing N-methylparoxetine comprising reacting CIPMA with sesamol-tetrabutylammonium salt in an organic solvent.

14. The process of claim 13, wherein the yield is at least about 25%.

15. The process of claim 14, wherein the yield is at least about 55%.

16. The process of claim 15, wherein the yield is at least about 85%.

17. The process of claim 13, wherein the organic solvent is selected from the group consisting of toluene and isopropyl alcohol.

18. The process of claim 13, wherein the organic solvent is a dipolar aprotic solvent.

19. The process of claim 18, wherein the dipolar aprotic solvent is acetonitrile.

20. A process for preparing paroxetine comprising removing the N-methyl group of N-methylparoxetine prepared by the process of claim 13.

21. The process of claim 20, wherein the N-methyl group is removed by transformation to a carbamate followed by alkaline hydrolysis.

22. An organic solvent consisting essentially of Sesamol tetrabutyl ammonium-salt in solution.

23. A process for preparing sesamol-tetrabutylammonium salt of claim 22 comprising contacting tetrabutylammonium ions with sesamol or sesamol ions in an organic solvent.

24. The process of claim 23, further comprising contacting in the presence of a base.

25. The process of claim 23, wherein the tetrabutylammonium ions are complexed with hydroxide ions.

26. The process of claim 23, wherein the organic solvent is an alcohol or a mixture of alcohols.

27. The process of claim 26, wherein the mixture comprises of isopropanol and methanol.

28. A process for preparing paroxetine comprising the step of reacting CIPMA with sesamol-tetrabutylammonium salt in an organic solvent to obtain an intermediate, and converting the intermediate to paroxetine.

29. The process of claim 28, further comprising converting the paroxetine to a hydrochloride salt.

30. A residue of sesamol tetrabutyl ammonium salt prepared by evaporation of the organic solvent of claim 22.

31. A process for preparing paroxetine comprising the step of reacting the Sesamol-tetrabutylammonium salt of claim 30 with CIPMA in acetonitrile, toluene or isopropanol to obtain an intermediate, and converting the intermediate to paroxetine.

32. The process of claim 31, further comprising converting the paroxetine to a hydrochloride salt.

33. The process of claim 1, wherein stereochemistry of compound (VII) is the same as the stereochemistry of paroxetine.

\* \* \* \* \*